US012629039B2

(12) United States Patent
Alessi et al.

(10) Patent No.:  US 12,629,039 B2
(45) Date of Patent:  May 19, 2026

(54) SENSORIZED EARPHONE DEVICE FOR OUT-OF-EAR MEASUREMENTS

(71) Applicant: STMicroelectronics S.r.l., Agrate Brianza (IT)

(72) Inventors: Enrico Rosario Alessi, Catania (IT); Enri Duqi, Milan (IT); Fabio Passaniti, Syracuse (IT)

(73) Assignee: STMicroelectronics S.r.l., Agrate Brianza (IT)

( * ) Notice: Subject to any disclaimer, the term of this patent is extended or adjusted under 35 U.S.C. 154(b) by 250 days.

(21) Appl. No.: 18/243,361

(22) Filed: Sep. 7, 2023

(65) Prior Publication Data

US 2024/0081660 A1     Mar. 14, 2024

(30) Foreign Application Priority Data

Sep. 8, 2022    (IT) ......................... 102022000018342

(51) Int. Cl.
*A61B 5/0205*       (2006.01)
*A61B 5/00*         (2006.01)
(Continued)

(52) U.S. Cl.
CPC ........ *A61B 5/02055* (2013.01); *A61B 5/0008* (2013.01); *A61B 5/0022* (2013.01); (Continued)

(58) Field of Classification Search
CPC . A61B 5/02055; A61B 5/0008; A61B 5/0022; A61B 5/01; A61B 5/6817; (Continued)

(56) References Cited

U.S. PATENT DOCUMENTS

| 11,839,451 B2 * | 12/2023 | Montgomery, II ... | G01L 9/0052 |
| 2016/0242731 A1 * | 8/2016 | Gharibian .............. | A61B 7/045 |

(Continued)

FOREIGN PATENT DOCUMENTS

| CN | 109729473 A | | 5/2019 | |
| CN | 110115567 A | * | 8/2019 | ......... A61B 5/14552 |
| WO | WO-2021150148 A1 | * | 7/2021 | ............. A61B 5/363 |

OTHER PUBLICATIONS

IT Search Report and Written Opinion for priority application, IT Appl. No. 102022000018342, report dated Apr. 12, 2023, 6 pgs.

(Continued)

*Primary Examiner* — Jonathan T Kuo
(74) *Attorney, Agent, or Firm* — Crowe & Dunlevy LLC

(57)                ABSTRACT

An earphone device has a casing having a measurement portion dedicated to acquisition of at least one measurement quantity with the earphone device arranged outside an ear of a subject. The earphone device is provided with at least one sensor, operatively coupled to the measurement portion within the casing for acquiring signals indicative of the measurement quantity, and a processing module that processes the signals acquired by the sensor so as to provide a processed output signal for monitoring the measurement quantity, as a function of the acquired signals. Electrical-connection elements define electrical paths within the casing in electrical connection with the sensor.

17 Claims, 3 Drawing Sheets

(51) Int. Cl.
   *A61B 5/01*          (2006.01)
   *H04R 1/10*          (2026.01)
(52) U.S. Cl.
   CPC .............. *A61B 5/01* (2013.01); *A61B 5/6817*
         (2013.01); *A61B 5/6824* (2013.01); *A61B*
            *2560/045* (2013.01); *A61B 2560/0468*
      (2013.01); *A61B 2562/0233* (2013.01); *A61B*
            *2562/0257* (2013.01); *A61B 2562/028*
         (2013.01); *A61B 2562/166* (2013.01); *H04R*
            *1/1016* (2013.01); *H04R 2420/07* (2013.01)
(58) Field of Classification Search
   CPC ............ A61B 5/6824; A61B 2560/045; A61B
            2560/0468; A61B 2562/0233; A61B
            2562/0257; A61B 2562/028; A61B
         2562/166; A61B 5/1102; A61B 5/6898;
         A61B 5/02438; H04R 1/1016; H04R
                                    2420/07
   See application file for complete search history.

(56)                References Cited

U.S. PATENT DOCUMENTS

| | | |
|---|---|---|
| 2019/0098388 A1 | 3/2019 | Powell et al. |
| 2019/0346934 A1 | 11/2019 | Schrader et al. |
| 2021/0352395 A1 | 11/2021 | Wang et al. |
| 2022/0087551 A1* | 3/2022 | Montgomery, II ..... G06F 1/169 |

OTHER PUBLICATIONS

Andreozzi, Emilio, et al.: "Forcecardiography: A Novel Technique to Measure Heart Mechanical Vibrations onto the Chest Wall," Sensors 2020, doi:10.3390/s20143885, 15 pgs.

* cited by examiner

SENSORIZED EARPHONE DEVICE FOR OUT-OF-EAR MEASUREMENTS

PRIORITY CLAIM

This application claims the priority benefit of Italian Application for Patent No. 102022000018342, filed on Sep. 8, 2022, the content of which is hereby incorporated by reference in its entirety to the maximum extent allowable by law.

TECHNICAL FIELD

This application relates to a sensorized earphone device for out-of-ear measurements.

BACKGROUND

The current trend of developing electronic systems for monitoring the physical condition or health of users at any moment of their life is well known; in particular, the aim is to develop inexpensive portable devices possibly having a high accuracy and being able to implement continuous monitoring with low consumption levels, considering the fact that the same devices are typically battery supplied.

For instance, physiological quantities that may be monitored regarding the health of users may include: heart rate (HR) and heart-rate variability (HRV); electrocardiogram (ECG); oxygen saturation in the blood ($SpO_2$), exploiting, for example, a photoplethysmography (PPG) technique with infrared radiation (IR) on the wrist or other positions of the body; blood pressure using non-invasive techniques, for example radiofrequency techniques or in a way derived from PPG and ECG measurements; and body temperature by sensors exploiting the emissions of the human body in the infrared spectrum.

More recently, as may be seen, for example, in Andreozzi, et al. "Forcecardiography: A Novel Technique to Measure Heart Mechanical Vibrations onto the Chest Wall", Sensors (Basel) vol. 20 (14), 3885, Jul. 13, 2020, an innovative technique, forcecardiography (FCG), has been proposed for monitoring the mechanical performance of the heart, based on the use of force sensors applied on the chest of a subject, e.g. by a strap. Such force sensors acquire the vibrations associated with the contraction of the cardiac muscle for the purposes of monitoring the mechanical performance of the same cardiac muscle (for example, for detection of the heart rate and of its variability). This Andreozzi, et al. reference is incorporated by reference in its entirety.

Devices that may be used for monitoring one or more of the aforesaid quantities are, for example, smart bracelets or watches, smart straps or patches, or even earphones or similar biometric acoustic apparatuses.

It is underlined, in particular, that devices of a known type are designed to implement measurements and corresponding processing locally in the area or region of the body where the devices themselves are applied (for example, on the wrist in the case of smart watches or bracelets, or inside or at the entrance to the auditory canal in the case of earphones).

With particular reference to earphone devices or the like, it is common to integrate sensors such as capacitive sensors or other types of sensors such as proximity or contact sensors. When connected to a portable electronic device, such as a smartphone, tablet, or the like, these sensors implement (single or multiple) touch activated functions, such as the control of the reproduction of music or of a telephone conversation. The aforesaid sensors may also be used to obtain information useful for purposes of compensation or the like, for example for filtering noise due to user movement.

It has also been proposed, as may be seen, for example, in Poh, et al., "Cardiovascular Monitoring Using Earphones and a Mobile Device", IEEE Pervasive Computing 11(2012): 18-26, the use of earphones for acquiring plethysmography measurements within the ear for the purposes of cardiovascular monitoring. In particular, the earphones are in this case sensorized with a reflection photosensor, designed to detect volumetric changes in the blood vessels during the cardiac cycle. This Poh, et al. reference is incorporated by reference in its entirety.

Nevertheless, further development is required.

SUMMARY

The aim of the present disclosure is to provide a monitoring solution, in particular for monitoring physiological quantities indicative of the physical conditions or health of a subject, being an alternative to, in particular an improvement of, known solutions.

In an embodiment, an earphone device includes a casing with a measurement portion. This measurement portion acquires at least one measurement quantity, relating to the earphone device when arranged outside an ear of a user. Included in the device is at least one sensor, which is operatively connected to the measurement portion within the casing. This sensor acquires signals indicative of the measurement quantity. The device also incorporates a processing module that processes the signals acquired by the sensor, providing a processed output signal for monitoring of this measurement quantity, as a function of the acquired signals. The design includes electrical-connection elements that define electrical paths within the casing, connected to the sensor.

The measurement portion of the device configured to be arranged in contact with a user's wrist. The sensor in this device, which may be a force sensor, measures force as a function of vibrations associated with the contraction of cardiac muscle of the user, a feature which is used for cardiorespiratory monitoring.

This earphone device may also include a control module that regulates the operation of the device. However, the measurement quantity captured by the sensor may in some instances not influence this operation. The electrical-connection elements of this device include a flexible printed-circuit board, with the electrical paths configured for connection between the sensor and the control module.

The measurement quantity captured by the device may be a physiological quantity associated with the user, aimed at monitoring the user's physical condition and/or health state. The device may also contain a detection module that automatically determines the start of the acquisition of the measurement quantity by the sensor and processing by the processing module. This determination may be made following the detection of a condition of proximity to, or contact with, the user's body, with the earphone device completely out-of-ear.

This detection module may include at least one detection electrode arranged outside the casing, corresponding to or in proximity to the measurement portion, so as to face the body of the user during measurement. The detection module may detect a variation of local charge due to proximity to, or contact with, the user's body, subsequently issuing a trigger signal for the start of acquisition and processing of the measurement quantity.

The measurement portion may be a reduced-thickness section of the base of the casing, internally forming a recess designed to house the sensor. This reduced-thickness section may serve as a flexible membrane designed to convert external pressure into a force applied to the sensor. The sensor may be a MEMS sensor and include a die of semiconductor material, with a main surface featuring a sensitive area facing the reduced-thickness portion. The casing of the device may also include a projecting element extending from the reduced-thickness portion towards the sensitive area, concentrating the external pressure on this sensitive area.

The sensor may be housed within the casing by a supporting plate, connected at an end portion to the electrical-connection elements. These electrical-connection elements may include a flexible printed-circuit board, which extends transversely with respect to the supporting plate and incorporates a reinforcement element in the area of coupling with the supporting plate. This reinforcement element may provide stiffening and serves as a mechanical stopper for the sensor.

In one configuration, the sensor may be an infrared body-temperature sensor. In this instance, a hole may be made in the casing at the measurement portion, closed by a lens that is transparent to infrared radiation. This sensor may be arranged in the casing beneath the lens. In another configuration, the sensor may be a contact temperature sensor mounted on a printed-circuit board, with a thermally conductive material arranged between the printed-circuit board and the measurement portion of the casing.

The earphone device may be configured to provide the acquired signals and/or processed output signal to an external electronic apparatus. This apparatus may feature a display designed to display the results of processing and/or analysis of the acquired signals, or other information associated with these signals.

The processing module may be designed to be operatively coupled to another earphone device carried by the user. This enables communication to the user of information regarding the execution of the force measurement via sound communication.

Finally, an electronic system for acquisition of at least one out-of-ear measurement quantity has been described. This system may include an earphone device, as previously detailed, and an electronic apparatus. The electronic apparatus includes a display designed to exhibit the results of processing and/or analysis of the acquired signals, or other information associated with these signals.

BRIEF DESCRIPTION OF THE DRAWINGS

For a better understanding, embodiments thereof are now described, purely by way of non-limiting example, with reference to the attached drawings, wherein.

DETAILED DESCRIPTION

Figure 1:
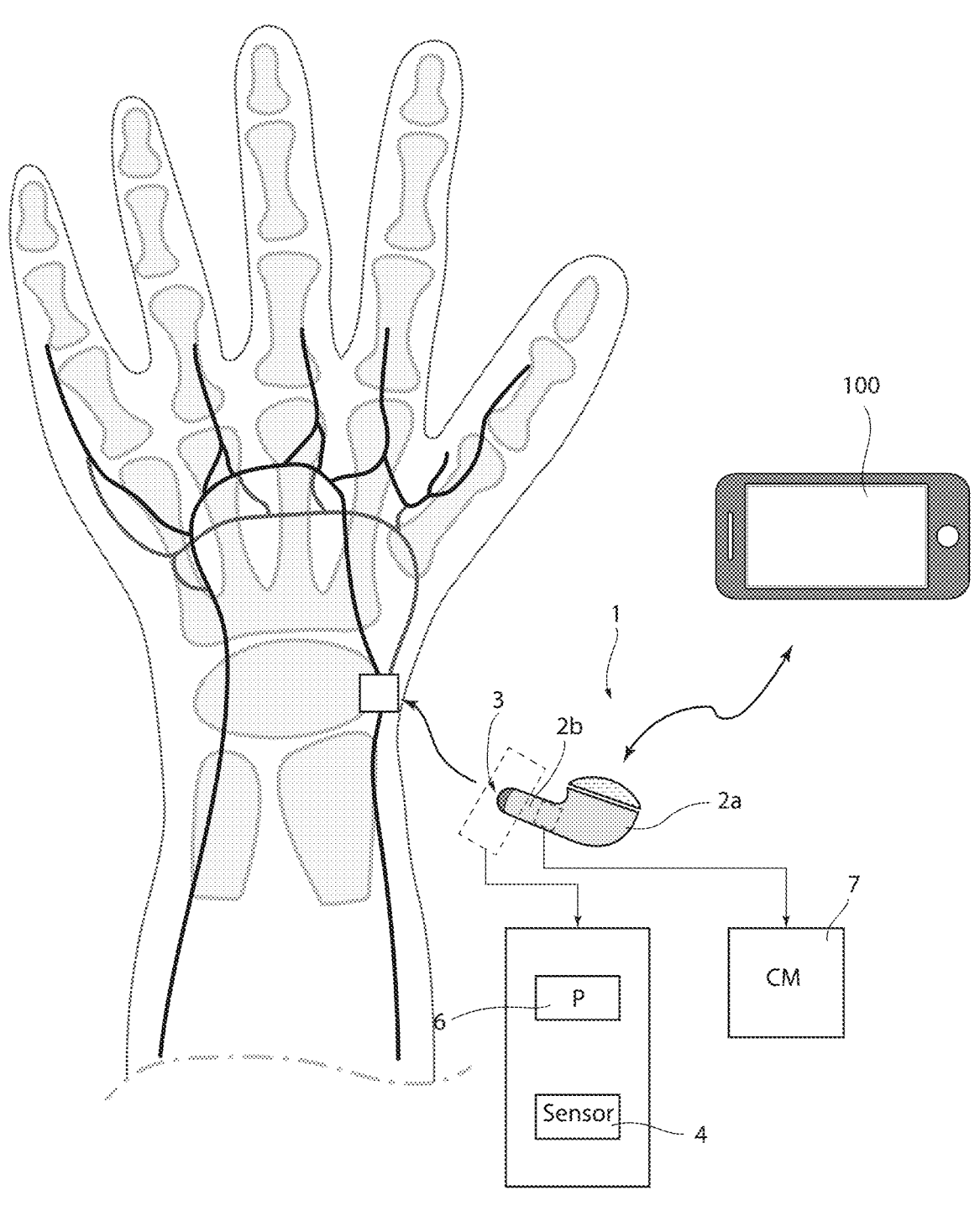
FIG. 1 is a schematic depiction of an earphone device, according to an aspect of the present disclosure, in an application for monitoring the health conditions of a subject.

As will be described in detail, one aspect of the present disclosure provides an earphone device, designated as a whole by 1 in FIG. 1, appropriately sensorized and configured so as to be used for measurements of quantities, in particular (but not only) of a physiological type, exclusively out of the ear (i.e., outside the standard area of application of the earphone device 1). Such quantities may or may not be associated with the standard operation of the earphone device 1, i.e., operations of sound reproduction for the user according to an operating state of the same earphone device 1.

The earphone device 1 otherwise has the functions usually envisaged for such devices, comprising a speaker for transducing electrical signals into the vibration of a diaphragm for generation of sound waves as a function of received electrical signals.

For instance, and as illustrated schematically, such electrical signals may be received with a wireless communication from an electronic apparatus 100 (for example, a smartphone, a tablet, or a portable PC), operatively coupled to the same earphone device 1.

In particular, the earphone device 1 comprises a casing 2, exposed to the external environment and made, for example, of polyvinylchloride (PVC).

This casing 2 comprises: a head part 2a, which defines a housing for a speaker (not illustrated) and is designed to be inserted into the ear, in the proximity or within the auditory canal; and a tip part 2b, which typically forms a portion for handling of the earphone device 1 by a user and may further carry one or more sensors (for example, contact or proximity sensors, not illustrated herein) to detect a touch exerted by the user and enable activation of functions of the earphone device 1 (such as, pausing or resumption of sound reproduction).

According to one aspect of the present disclosure, the aforesaid casing 2 further comprises a measurement portion 3, dedicated to detection of at least one measurement quantity. In the embodiment illustrated in FIG. 1, this measurement portion 3 is designed to be arranged in contact with a part of the body of a subject, in particular in contact with the wrist in a position corresponding to the radial artery.

In this embodiment, the earphone device 1 is configured to carry out a force measurement for acquisition (according to the aforementioned forcecardiography technique) of a signal associated with cardiorespiratory monitoring of the subject, in particular for monitoring physiological quantities that may include the heart rate (HR) and/or the heart-rate variability (HRV).

The earphone device 1 comprises, within the casing 2, operatively coupled to the aforesaid measurement portion 3, at least one sensor 4 (represented schematically in the aforesaid FIG. 1), for example of a MEMS (Micro-Electro-Mechanical System) type, configured to implement the detection of the aforesaid measurement quantity.

The measurement portion 3 may be designed and configured to provide for a level of resistance against intrusion by water or other liquid, providing for sealing with respect to the external environment.

In the embodiment illustrated in FIG. 1, the sensor 4 is a force sensor, configured to acquire a monitoring signal (so-called FCG signal) as a function of the vibrations associated with the contraction of the cardiac muscle (this monitoring signal may be indicative of the heart rate, the heart-rate variability and/or one or more other physiological parameters).

As shown schematically, the earphone device 1 comprises a processing circuit (P) 6 within the casing 2, configured to process the acquired signals and supply a processed output signal, as a function of the same acquired signals.

The above processing circuit 6 may, for example, be integrated in the same sensor 4, for instance in the form of an ASIC (Application-Specific Integrated Circuit), within a die or package of the aforesaid sensor 4.

Alternatively, the processing circuit 6 may form part of, or be implemented by, a control module (CM) 7 housed in the casing 2 of the earphone device 1, for example including a microcontroller, a microprocessor, or a similar digital processing unit, having the function of managing and controlling general operation of the earphone device 1. This management and control may be of, for example, the reproduction of sounds as a function of received signals, the state of one or more switch elements, or the spatial position of the earphone device 1 (in particular, its proximity to the ear). In this case, appropriate electrical conductive paths are provided within the casing 2, for connection of the aforesaid sensor 4 to the control module 7.

In any case, it is underlined that the measurement quantity is not used by the control module for controlling the operation of the earphone device 1.

Alternatively, at least part of the processing of the signals acquired by the sensor 4 may be implemented externally to the casing 2 and generally to the earphone device 1, which has an appropriate communication interface, in particular of a wireless type, for communication of the acquired signals to a system external to the casing 2, for example towards the afore said electronic apparatus 100.

Figure 2:
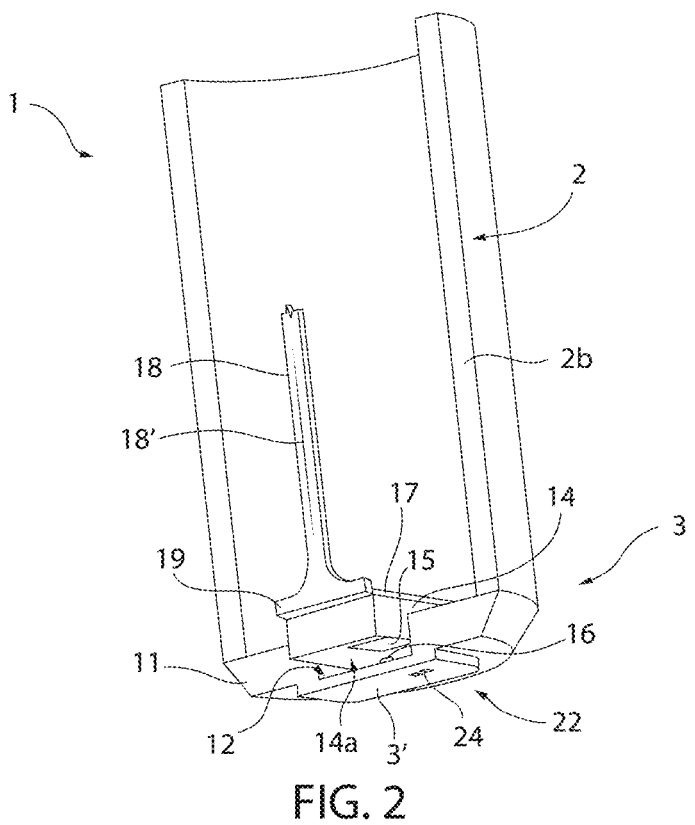
FIG. 2 is a sectioned perspective view of a portion of the earphone device in one embodiment of the present disclosure.
Figure 3:
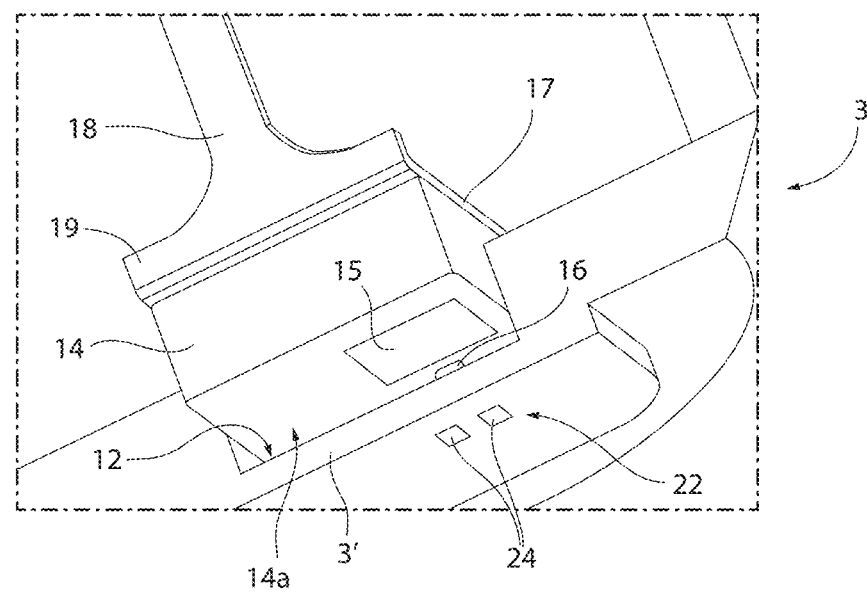
FIG. 3 shows an enlarged portion of the earphone device of FIG. 2.

In greater detail, and with reference to FIGS. 2 and 3, a possible embodiment of the earphone device 1 is now described, related to use for measurement of the heart rate, heart-rate variability, and/or other physiological parameters, by a high-sensitivity force sensor and an appropriate mechanism of mechanical coupling to the subject, in particular on the wrist (a different measurement position may, however, be considered).

The measurement portion 3 of the casing 2 of the earphone device 1 is in this case arranged at a distal end of the tip part 2*b* of the same earphone device 1 that is arranged at a greater distance from the head part 2*a*.

In this embodiment, the aforesaid measurement portion 3 comprises a reduced-thickness portion 3' of a base 11 of the aforesaid casing 2, which internally defines a recess 12, designed to house the sensor 4. This reduced-thickness portion 3' defines a flexible membrane, designed to convert an external pressure into a force applied to the sensor 4 (as also discussed in greater detail hereinafter).

In the example illustrated in FIGS. 2 and 3, the reduced-thickness portion 3' projects from the surface of the base 11 of the casing 2 so as to clearly define for the user the area where the measurements are to be performed (in particular, the area that is to rest on the wrist of the subject). In a possible implementation, the projecting part of the measurement portion 3 has a diameter of approximately 3 mm, to facilitate mechanical coupling to the radial artery.

The aforesaid sensor 4 is, as mentioned previously, a high-sensitivity force sensor, for example having a resolution (understood as the minimum variation of the force detectable by the sensor) of less than 0.1 mN.

For instance, the above force sensor may be made as described in United States Patent Publication No. 2017/0343430, the contents of which are incorporated by reference in their entirety.

In particular, the sensor 4 is made in a die 14 of semiconductor material, for example silicon, having a main surface 14*a*, facing, with a certain gap, the aforesaid reduced-thickness portion 3', where a sensitive area 15 of the force sensor is provided (having an extension smaller than the corresponding extension of the aforesaid main surface 14*a*).

Consequently, the earphone device 1 comprises, at the aforesaid measurement portion 3, a projecting element 16, for example in the form of a thin tip, which extends from the reduced-thickness portion 3' towards the aforesaid sensitive area 15 so as to concentrate the external pressure on the sensitive area 15 and amplify the force exerted.

In greater detail, the sensor 4 is carried within the casing 2 by a supporting plate 17, coupled, at an end portion thereof, to a flexible PCB 18, which defines electrical paths (designated as a whole by 18') for electrical connection of the sensor 4 to the control module 7 (here not illustrated) and transmission of the acquired signals and/or of the processed output signal (according to whether the processing of the acquired signals by the processing circuit 6 is implemented inside or outside the sensor 4).

In the embodiment illustrated, the aforesaid flexible PCB 18 extends in a transverse direction with respect to the supporting plate 17 and has, in the area of coupling to the supporting plate 17, a reinforcement part 19 having a stiffening function and operating as a mechanical stopper for the sensor 4, preventing displacement thereof within the casing 2 upon application of a strong force on the measurement portion 3.

According to one aspect of the present disclosure, the earphone device 1 further comprises a detection module 22, configured to automatically determine the start (and possibly the end) of acquisition and processing of the measurement quantity by the sensor 4 and the associated processing circuit 6, in particular upon determination of a condition of proximity or contact with (or conversely of distancing from) the body of the user, when the earphone device 1 is completely out of the ear (in the example described previously, when the earphone device 1 is taken out of the ear and arranged in contact with the skin of the wrist to carry out cardiovascular monitoring).

The aforesaid detection module 22 is connected electrically to the processing circuit 6 or to the aforesaid control module 7 of the earphone device 1, or, alternatively, may be at least in part implemented by the same processing circuit 6 (possibly within the sensor 4) or by the control module 7.

In a possible embodiment, the detection module 22 comprises at least one detection electrode 24 (two of them are illustrated in FIG. 3), of a metal material (such as silver chloride, AgCl, or stainless steel), possibly coated with a layer of dielectric material, arranged outside the casing 2, in a position corresponding to, or in the proximity of, the measurement portion 3, in particular at the aforesaid reduced-thickness portion 3', so as to be arranged facing the body of the user during execution of the measurements.

In a possible implementation, the detection module 22 is configured to detect a variation of local charge (and a consequent variation of electrical field and potential) due to the proximity to or contact with the body of the user and consequently to issue a trigger signal for the start (or stop) of acquisition and processing of the measurement quantity.

Figure 4:
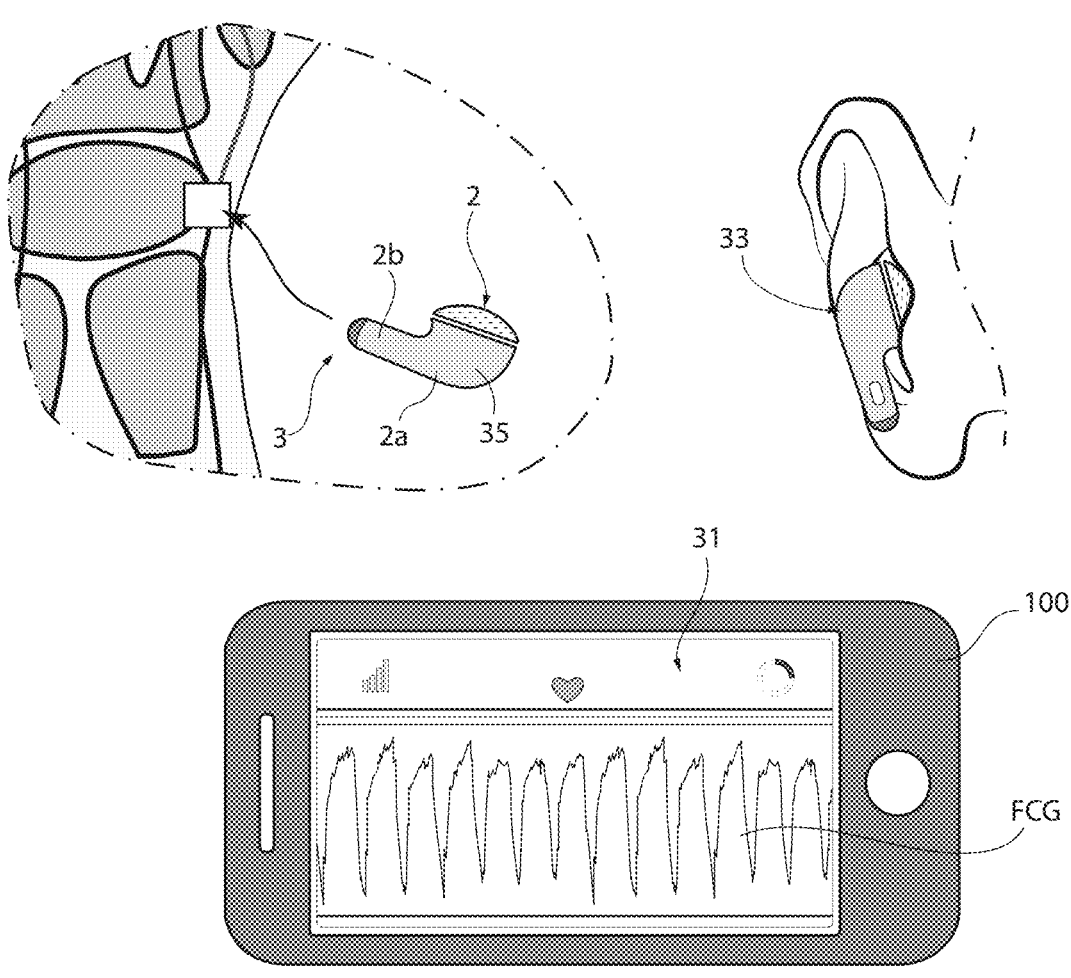
FIG. 4 shows an exemplary use of the earphone device.

FIG. 4 is a schematic illustration of a possible situation of use of the earphone device 1, in a condition of acquisition of the measurement quantity, in the example once again for acquisition of the FCG signal on the wrist of a subject.

The earphone device 1 is shown operatively coupled, in a wireless mode, in particular with TWS (True Wireless Stereo) technology, to the electronic apparatus 100, which is for example of a portable type, such as a smartphone or a tablet, or a wearable type, such as a smart watch or bracelet.

In a possible implementation, instructions for execution of the measurement may be provided to a user on a display 31 of the aforesaid electronic apparatus 30; furthermore, on the same display 31 results or further information regarding processing and/or analysis of the signal acquired by the processing circuit 6 (and/or the control module 7) may be provided.

For instance, as illustrated in the same FIG. 4, a time plot of the FCG signal acquired or further information associated with the same signal acquired may be shown on the display 31.

According to a further aspect of the present disclosure, alternatively, or in addition, instructions for execution of the measurement (or other information associated with the same measurement) may be provided to the user via a sound communication (for example, by voice synthesis or other similar tools) through a further earphone device, designated by 33 in FIG. 3, inserted into the ear of the user and forming, together with the earphone device 1, a pair of earphones.

In this case, intervention of the aforesaid electronic apparatus 100 may even not be envisaged, since management of the communication with the user may be implemented entirely by the aforesaid processing circuit 6 and/or by the control module 7 of the earphone device 1, through a communication coupling with the further earphone device 33.

According to a further aspect of the present disclosure, one or more status LEDs (or similar display elements) 35 present outside the casing 2 of the earphone device 1 may be used to signal (for example, by being lit up, or with a particular intermittent flashing) acquisition of the measurement quantity or some other operating status of the earphone device 1 regarding the aforesaid operation of acquisition of the measurement quantity.

The advantages of the present disclosure emerge clearly from the foregoing description.

In any case, it is underlined that the disclosures herein provide for, in an inexpensive and simple way, the making of measurements of quantities, in particular of a physiological nature for monitoring the physical conditions or the health condition of a user, using devices (earphones) that are widely used in combination with portable electronic apparatuses.

This disclosure further enables advantageous exploitation of the same portable electronic apparatuses to facilitate execution of the measurements and/or display of information associated with the results of the same measurements.

Finally, it is clear that modifications and variations may be made to what has been described and illustrated herein, without thereby departing from the scope of the present invention, as defined in the appended claims.

In particular, it is underlined that further and different sensors may be provided for sensorization of the earphone device 1, and consequently acquisition of further and different quantities, for example of a physiological nature, may be envisaged.

In this regard, the aforesaid sensor 4 of the earphone device 1 may comprise an infrared body-temperature sensor.

In this case, the measurement portion 3 of the casing 2, which may also in this case be arranged at the distal end of the tip part 2b of the same casing 2, may include a hole made in the casing 2 (for example, having a depth of 0.5 cm) and a protective lens transparent to the infrared radiation, for example in the range of wavelengths comprised between 5 μm and 20 μm (corresponding to the frequency bandwidth of detection of the sensor 4). The sensor 4 may be in this case housed underneath this protective lens, within the casing 2. The optical characteristics of the protective lens may be adjusted based on the characteristics of the sensor 4.

In this example, the subject of which the body temperature is measured may be the user of the earphone device 1 or even a different person, on whom the measurement portion 3 of the earphone device 1 may be applied.

A further exemplary embodiment may envisage the use in the earphone device 1 of a contact temperature sensor.

In this case, the sensor 4 within the casing 2 may comprise a standard temperature sensor of an SMD (Surface-Mount Device) type, which may be mounted on a printed-circuit board, for example once again at the aforesaid distal end of the tip part 2b of the casing 2.

An appropriate thermally conductive material, for example in the form of a ring, may be arranged between the printed-circuit board and the measurement portion 3 of the casing 2 that is to be in contact with the subject to be measured so as to ensure a high thermal conductivity and thus guarantee fast response times.

It is again underlined that the arrangement of the aforesaid measurement portion 3 with respect to the casing 2 of the earphone device 1 may also vary with respect to what has been illustrated, even though the arrangement at the distal end of the tip part 2b of the casing 2 may prove advantageous for most measurement applications.

Figure 5:
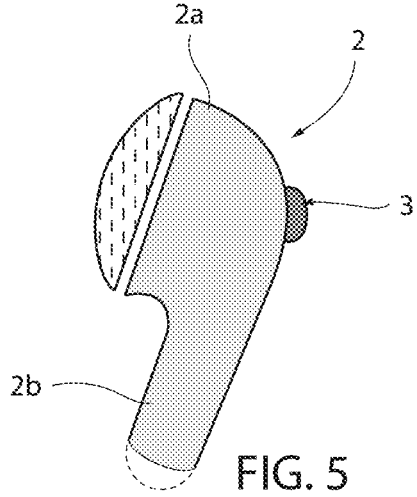
FIG. 5 is a schematic depiction of a variant embodiment of the earphone device, according to a further aspect of the present disclosure.

For instance, as illustrated schematically in FIG. 5, the measurement portion 3 may be provided at the head part 2a of the casing 2, with a projection in a direction opposite to the area where the speaker is housed, which area is to be inserted into the user's ear.

Moreover, it is once again underlined that the earphone device 1 may comprise further sensors coupled to the casing 2, for example the previously mentioned capacitive or proximity sensor for implementing touch (or tap) control functions.

The invention claimed is:

1. An earphone device, comprising:

a casing having a measurement portion configured to acquire at least one measurement quantity with respect to said earphone device being arranged outside an ear of a user;

at least one sensor operatively coupled to the measurement portion within the casing and configured to acquire signals indicative of said at least one measurement quantity;

a processing module configured to process the signals acquired by the at least one sensor, and configured to provide a processed output signal for monitoring of said at least one measurement quantity as a function of the acquired signals; and electrical-connection elements defining electrical paths within the casing and in electrical connection with the at least one sensor;

wherein said measurement portion is configured to be arranged in contact with a wrist of the user in a position corresponding to an artery, and wherein said at least one sensor is a force sensor configured to carry out a measurement of force as a function of vibrations associated with contraction of cardiac muscle of the user for cardiorespiratory monitoring.

2. The earphone device according to claim 1, further comprising a control module configured to control operation of said earphone device, wherein said at least one measurement quantity is not used by said control module for controlling operation of said earphone device.

3. The earphone device according to claim 2, wherein said electrical-connection elements comprise a flexible printed-circuit board and said electrical paths are configured for electrical connection of said at least one sensor to said control module.

4. The earphone device according to claim 1, wherein said at least one measurement quantity is a physiological quantity associated with said user for monitoring a physical condition of the user and/or a state of health of the user.

5. The earphone device according to claim 1, further comprising a detection module configured to automatically determine a start of acquisition of the at least one measurement quantity by the at least one sensor and processing by the processing module, following determination of a condition of proximity to, or contact with, a body of the user, with the earphone device completely out-of-ear.

6. The earphone device according to claim 5, wherein said detection module comprises at least one detection electrode arranged outside the casing in a position corresponding to, or in the proximity of, the measurement portion so as to be arranged facing a body of the user during execution of the measurement; and said at least one detection electrode being configured to detect a variation of local charge due to the proximity to, or contact with, the body of the user and consequently to issue a trigger signal for start of acquisition and processing of the at least one measurement quantity.

7. The earphone device according to claim 1, wherein said measurement portion is a reduced-thickness portion of a base of the casing, internally defining a recess, designed to house said at least one sensor, said reduced-thickness portion defining a flexible membrane designed to convert an external pressure into a force applied to the at least one sensor.

8. The earphone device according to claim 7, wherein said at least one sensor is a MEMS sensor and comprises a die of semiconductor material, having a main surface with a sensitive area facing the reduced-thickness portion; and wherein said casing further comprises, at the measurement portion, a projecting element which extends from the reduced-thickness portion towards said sensitive area so as to concentrate the external pressure on said sensitive area.

9. The earphone device according to claim 6, wherein the at least one sensor is carried within the casing by a supporting plate coupled, at an end portion thereof, to said electrical-connection elements; and wherein said electrical-connection elements comprise a flexible printed-circuit board which extends in a direction transverse with respect to the supporting plate and has, in an area of coupling with said supporting plate, a reinforcement element having a function of stiffening and mechanical stopper for the at least one sensor.

10. The earphone device according to claim 1, wherein said at least one sensor is an infrared body-temperature sensor; wherein a hole is defined in the casing at said measurement portion, the hole being closed by a lens transparent to infrared radiation; and said at least one sensor being arranged in the casing underneath said lens.

11. The earphone device according to claim 1, wherein said at least one sensor is a contact temperature sensor and is mounted on a printed-circuit board with a thermally conductive material being arranged between said printed-circuit board and the measurement portion of the casing.

12. The earphone device according to claim 1, configured to provide the acquired signals and/or processed output signal to an electronic apparatus external to said earphone device and having a display designed to display results of processing and/or analysis of the acquired signals or other information associated with said acquired signals.

13. The earphone device according to claim 1, wherein said processing module is configured to be operatively coupled to a further earphone device carried by said user for communication to the user of information regarding execution of the measurement of force via a sound communication.

14. An electronic system for acquisition of at least one out-of-ear measurement quantity, comprising:
the earphone device according to claim 1; and
an electronic apparatus, wherein the electronic apparatus has a display designed to display results of processing and/or analysis of the acquired signals or other information associated with said acquired signals.

15. An earphone device configured for measurements of physiological quantities of a user, the earphone device comprising:
a casing comprising a head part defining a housing for a speaker, a tip part for handling by a user, and a measurement portion configured to acquire at least one measurement quantity with respect to said earphone device being arranged outside an ear of a user, wherein said measurement portion is arranged to be in contact with a part of a body of the user associated with a radial artery;
at least one sensor within said tip part and configured to acquire signals indicative of the at least one measurement quantity; and
a processing circuit within said tip part and configured to process signals acquired from said at least one sensor and output a processed signal based thereupon.

16. The earphone device of claim 15, wherein the at least one sensor is a force sensor configured to acquire a monitoring signal indicative of one or more of: heart rate, heart-rate variability, and/or other physiological parameter of the user.

17. The earphone device of claim 15, further comprising a detection module configured to determine start and end of acquisition and processing of the at least one measurement quantity based on a condition of proximity or contact with the body of the user.

* * * * *